US009816077B2

(12) United States Patent
Kolot et al.

(10) Patent No.: US 9,816,077 B2
(45) Date of Patent: Nov. 14, 2017

(54) USE OF INTEGRASE FOR TARGETED GENE EXPRESSION

(75) Inventors: Mikhail Kolot, Gan Yavne (IL); Ezra Yagil, Ramat Hasharon (IL); Natalia Malchin, Tel-Aviv (IL)

(73) Assignee: RAMOT AT TEL-AVIV UNIVERSITY LTD., Tel-Aviv (IL)

( * ) Notice: Subject to any disclaimer, the term of this patent is extended or adjusted under 35 U.S.C. 154(b) by 0 days.

(21) Appl. No.: 14/236,714

(22) PCT Filed: Aug. 1, 2012

(86) PCT No.: PCT/IL2012/050286
§ 371 (c)(1),
(2), (4) Date: Feb. 3, 2014

(87) PCT Pub. No.: WO2013/018096
PCT Pub. Date: Feb. 7, 2013

(65) Prior Publication Data
US 2014/0171494 A1 Jun. 19, 2014

Related U.S. Application Data

(60) Provisional application No. 61/514,512, filed on Aug. 3, 2011.

(51) Int. Cl.
*C12N 9/12* (2006.01)
*A61K 38/16* (2006.01)
*C12N 15/85* (2006.01)
*C12N 15/86* (2006.01)

(52) U.S. Cl.
CPC .......... *C12N 9/1241* (2013.01); *A61K 38/164* (2013.01); *C12N 15/85* (2013.01); *C12N 15/86* (2013.01); *C12N 2740/16043* (2013.01); *C12N 2800/30* (2013.01); *C12N 2830/008* (2013.01)

(58) Field of Classification Search
None
See application file for complete search history.

(56) References Cited

U.S. PATENT DOCUMENTS

| 7,670,823 | B1 | 3/2010 | Hartley |
| 7,732,585 | B2 | 6/2010 | Calos |
| 2003/0027337 | A1 | 2/2003 | Droge |
| 2004/0003420 | A1* | 1/2004 | Kuhn ................. A01K 67/0275 800/14 |
| 2010/0299771 | A1* | 11/2010 | Kuhn et al. ..................... 800/18 |

FOREIGN PATENT DOCUMENTS

| WO | 2001/007572 | A2 | 2/2001 |
| WO | 2001/038511 | A2 | 5/2001 |
| WO | 2006/047227 | A1 | 5/2006 |

OTHER PUBLICATIONS

Lasko et al., Targeted oncogene activation by site-specific recombination in transgenic mice; PNAS, vol. 89, pp. 6323-6236, 1992.*
Abdul-Ghani et al., Use of Transcriptional Regulatory Sequences of Telomerase (hTER and hTERT) for Selective Killing of Cancer Cells; Molecular Therapy, vol. 2, No. 6, pp. 539-544, 2000.*
Kolot, M., Site-specific recombination in human cells catalyzed by the wild-type integrase protein of coliphage HK022; Biotechnology and Bioengineering, vol. 84, No. 1, pp. 56-60, 2003.*
Azaro and Landy Lamnbda Integrase and the Lamnbda int family. In: Mobile DNAII. Craig NL, Craigie R, Gellert M and Lambowitz A (eds). Washington DC: ASM Press, pp. 118-148 (2002).
Gottfried et al.,Site-specific recombination in *Arabidopsis* plants promoted by Integrase protein of coliphage HK022. Plant Molecular Biology 57: 435-444 (Feb. 2005).
Harel-Levi et al., Human genomic site-specific recombination catalyzed by coliphage HK022 integrase. J Biotechnol 134: 46-54 (Mar. 2008).
Kanegae et al., High-level expression by tissue/cancer-specific promoter with strict specificity using a single-adenoviral vector. Nucleic Acids Res 39(2): e7 (online Nov. 2010).
Malchin et al., Optimization of coliphage HK022 Integrase activity in human cells. Gene 437(1-2): 9-13 (May 2009).
Melnikov et al., Site-Specific Recombination in the *Cyanobacterium anabaena* sp Strain PCC 7120 Catalyzed by the Integrase of Coliphage HK022. Journal of Bacteriology 191: 4458-4464 (Jul. 2009).
Nagy, Cre recombinase: the universal reagent for genome tailoring. Genesis 26(2): 99-109 (2000).
Sotomayor et al., Role of tumor-derived cytokines on the immune system of mice bearing a mammary adenocarcinoma. II. Downregulation of macrophage-mediated cytotoxicity by tumor-derived granulocyte-macrophage colony-stimulating factor. J Immunol 147: 2816-23 (Oct. 1991).
Weisberg et al., Family values in the age of genomics: comparative analyses of temperate bacteriophage HK022. Annu Rev Genet 33: 565-602 (Dec. 1999).
M-C Keogh, D Chen, JF Schmitt, U Dennehy, VV Kakkar and NR Lemoine (1999) Design of a muscle cell-specific expression vector utilising human vascular smooth muscle a-actin regulatory elements. Gene Therapy (1999) 6, 616-528.
C Lefevre, M Imagawa, S Dana, J Grindlay, M Bodner, and M Karin (1987). Tissue-specific expression of the human growth hormone gene is conferred in part by the binding of a specific trans-acting factor. EMBO J. Apr. 1987; 6(4): 971-981.
Dong Liu and Itzhak Fischer (1996) Two Alternative Promoters Direct Neuron-Specific Expression of the Rat Microtubule-Associated Protein 1B Gene. The Journal of Neuroscience, Aug. 15, 1996, 16(16):5026-5036.
Adriana Heguy, Adrian West, Robert I. Richards, and Michael Karin (1986). Structure and Tissue-Specific Expression of the Human Metallothionein IB Gene. Molecular and Cellular Biology, Jun. 1986, 6(6):2149-2157.
Ito ,H., Kyo,S., Kanaya,T., Takakura,M., Inoue,M. and Namiki,M. (1998) Expression of human telomerase subunits and correlation with telomerase activity in urothelial cancer. Clin. Cancer Res., 4, 1603-1608.

(Continued)

Primary Examiner — Addison D Ault
(74) Attorney, Agent, or Firm — Browdy and Neimark, PLLC

(57) ABSTRACT

There are provided methods and compositions for activating the expression of an exogenous gene by an exogenous integrase specifically in cells in which the exogenous integrase is expressed. The invention further relates to uses of the compositions in treatment of various conditions and disorders, as exemplified by selectively activating expression of a toxin only in target cell populations.

17 Claims, 5 Drawing Sheets

(56) References Cited

OTHER PUBLICATIONS

Takakura, M., Kyo,S., Kanaya,T., Tanaka,M. and Inoue,M. (1998) Expression of human telomerase subunits and correlation with telomerase activity in cervical cancer. Cancer Res., 58, 1558-1561.

V K Gupta, J O Park, T Kurihara, A Koons, H J Mauceri, N T Jaskowiak, D W Kufe, R R Weichselbaum3and M C Posner (2003) Selective gene expression using a DF3/MUC1 promoter in a human esophageal adenocarcinoma model. Gene Therapy (2003) 10, 206-212. doi:10.1038/sj.gt.3301867.

Berry NB, Cho YM, Harrington MA, Williams SD, Foley J, Nephew KP. (2004) ranscriptional targeting in ovarian cancer cells using the human epididymis protein 4 promoter. Gynecol Oncol. Mar. 2004;92(3):896-904.

Tan K, Kajino K, Momose S, Masaoka A, Sasahara K, Shiomi K, Izumi H, Abe M, Ohtsuji N, Wang T, Hino O, Fujii H. (2010) Mesothelin (MSLN) promoter is hypomethylated in malignant mesothelioma, but its expression is not associated with methylation status of the promoter. Hum Pathol. Sep. 2010;41(9):1330-8. doi: 10.1016/j.humpath.2010.03.002. Epub Jun. 22, 2010.

\* cited by examiner

Figs. 5A-C

Figs. 6A-C
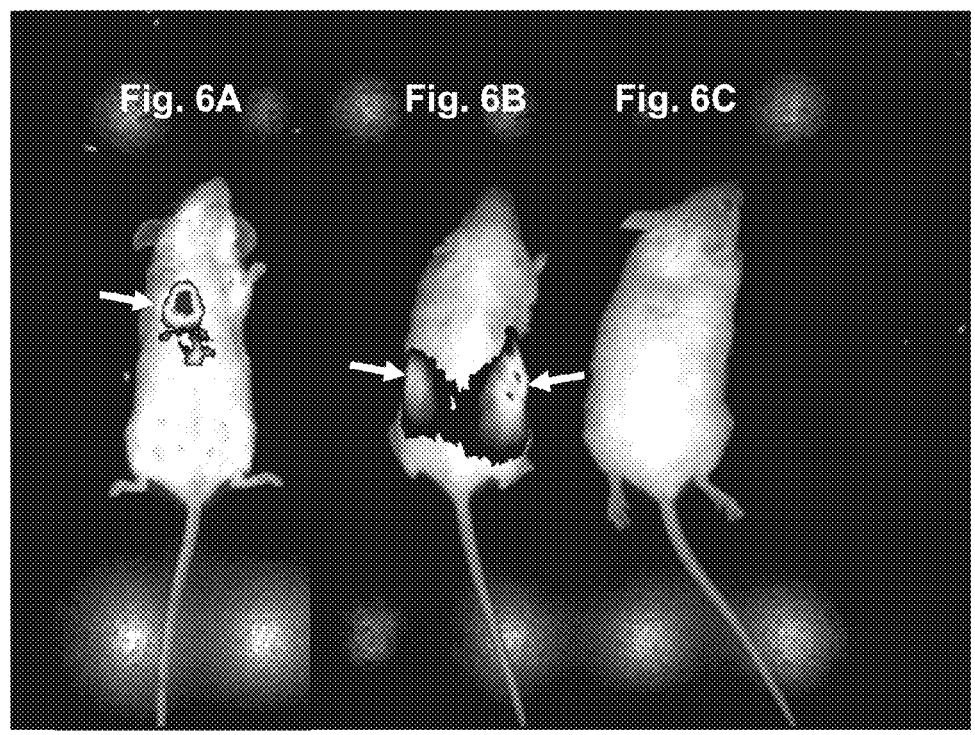

Figs.7A-B

USE OF INTEGRASE FOR TARGETED GENE EXPRESSION

FIELD OF THE INVENTION

The present invention relates to compositions for expressing an exogenous gene of interest by an exogenous integrase specifically in cells in which the exogenous integrase is expressed. The invention further relates to uses of the compositions in treatment of various conditions and disorders, as exemplified by selectively activating expression of an exogenous toxin only in target cell populations.

BACKGROUND OF THE INVENTION

Phage integrases are enzymes that mediate site-specific recombination between two DNA recognition sequences, the phage attachment site, attP, and the bacterial attachment site, attB. Typically, integrases are grouped into two major families based on their mode of catalysis. The tyrosine family integrases utilize a catalytic tyrosine to mediate strand cleavage, and some of them require accessory protein(s) for the reaction. The serine family integrases use a catalytic serine for strand cleavage.

Phage integrases mediate efficient site-specific recombination between two different sequences that are relatively short, enabling them to manipulate eukaryotic cells with large genomes, such as mammals.

The Integrase (Int) recombinase of the coliphage HK022 mediates integration and excision of the bacteriophage DNA into and out of a specific chromosomal site on its *Escherichia coli* host. These two site-specific recombination reactions occur between two defined pairs of DNA attachment (att) sites. The bacterial attB consists of a 21 base pair (bp) core sequence (BOB') that is composed of 7 central bps, defined as the overlap O (the site of DNA exchange), flanked by two 7 bp inverted repeats (B and B') that serve as binding sites for Int. The corresponding site on the phage chromosome attP is composed of a similar core (COC') that is flanked by two long arms (P and P' of 157 and 85 bps, respectively) carrying additional binding sites for Int and for the accessory DNA bending proteins (IHF, and Xis) that, in *E. coli*, are required for the reaction. When bivalent Int monomers and accessory proteins are bound to the P and P' arms of attP, the latter's bend the arms, thereby facilitating binding of the catalytic domain of Int to the core, the site of the reaction. Subsequently, this proteo-DNA complex (the intasome) captures attB to perform the recombination reaction. Phage excision occurs between the recombinant attL (BOP') and attR (POB') sites that flank the integrated prophage, each composed of the recombined core and one of the arms. Since the integration/excision reactions use a different pair of att sites and a different composition of the accessory proteins, they are not completely reversible (Weisberg et al., 1999; Azaro and Landy, 2002).

The wild type Int of HK022 was developed by some of the inventors of the present invention, to catalyze site-specific integration and excision of plasmid DNA into the human genome in cell cultures, as well as in *Arabidopsis* plants and *Anabaena* algae when supplied with the relevant att sites (Harel-Levy G. et al., 2008; Gottfried et al., 2005; Melnikov et al., 2009). In the eukaria, Int is active in integrative as well as in excisive reactions without the need to supply any of the accessory proteins (i.e. IHF and Xis), that are required for these reactions in *E. coli*. Nevertheless, it has been demonstrated by some of the inventors of the present invention that an int gene that was modified for optimal human codon usage and the presence of the accessory proteins significantly improved the recombination activities of Int in the human cells (Malchin et al., 2009).

U.S. Pat. No. 7,732,585 discloses a nucleic acid encoding an altered unidirectional site-specific bacteriophage integrase that has integrase activity, wherein said altered integrase has improved recombination efficiency towards wild-type or pseudo attachment sites as compared to a corresponding wild-type integrase.

U.S. Pat. No. 7,670,823 discloses an isolated nucleic acid molecule comprising a lambda att recombination site wherein a sequence of the seven base pair overlap region within the fifteen base pair core region is ATTATAC. It is further disclosed that the lambda att-recombination site is located between a transcriptional regulatory sequence and an open reading frame, wherein the transcriptional regulatory sequence and open reading frame are operably linked.

PCT Patent Application Publication No. WO2001/007572 discloses methods for obtaining integration of nucleic acids into eukaryotic cells. The publication discloses site-specific recombination systems that use prokaryotic recombinase polypeptides, such as the ΦC31 integrase, that can mediate recombination between the recombination sites, but not between hybrid recombination sites that are formed upon the recombination.

PCT Patent Application Publication No. WO2001/038511 discloses a method for the sequence-specific recombination of DNA in eukaryotic cells, comprising: introducing a first DNA sequence which contains a res sequence and copy of the first DNA sequence into a cell, and performing the sequence-specific recombination using the influence of a resolvase.

U.S. Patent Application Publication No. 2003/027337 discloses a method of sequence specific recombination of DNA in eukaryotic cells utilizing att sequences from the bacteriophage lambda. The publication further discloses a method comprising performing the sequence specific recombination of DNA with an Int and a Xis factor.

There remains an unmet need for compositions and methods enabling specific and efficient expression of exogenous genes of interest specifically in target cells and not in other cell populations.

SUMMARY OF THE INVENTION

The present invention provides novel compositions for expressing an exogenous gene of interest by an exogenous integrase specifically in cells in which both genes are expressed. In particular, the present invention discloses compositions comprising nucleic acid sequences encoding phage integrases for the expression of any desired gene in a target cell, wherein the integrase and the gene of interest are each regulated by a tissue specific promoter which may be activated only in the target cell. The methods and compositions of the invention are based in part on the discovery that a DNA construct comprising a dual promoter control system, namely one or more tissue specific promoters, that may be the same or different, each controlling the expression of a different nucleic acid sequence, enables a simple and very efficient method for expression of any desired exogenous gene of interest in a target cell. Advantageously, the dual promoter control system ensures that the exogenous gene of interest is expressed specifically in the target cell.

The compositions of the invention are also useful for therapeutic platforms for treating a disease or condition by selectively and specifically expressing genes of interest (and proteins) capable of eradicating the disease or condition in a desired target cell. A non-limiting example demonstrated herein below, shows that a DNA construct comprising the hTERT promoter, which is activated only in cancer cells regulates the expression of an HK022 integrase. In turn, the expressed HK022 integrase, excises a transcription terminator, which is located on the same DNA construct. The excision of said transcription terminator enables the expression of subunit A of the diphtheria toxin (DTA) which is under the regulation of a second hTERT promoter, thereby doubly ensuring the expression of DTA specifically in the cancer cells. Optionally, the methods of the invention may be used for tissue specific down regulation of genes by expressing relevant anti-sense gene fragments of the gene which is desired to be down-regulated.

Although the compositions of the invention are exemplified for cancer cells, the compositions are applicable, with suitable tissue promoters, for the expression of any desired gene in any target cell.

According to some embodiments, the present invention provides a composition comprising a nucleic acid sequence for expression of an exogenous gene of interest in a target cell co-expressing an exogenous integrase, wherein said nucleic acid sequence comprises:
  (a) a first sequence encoding the exogenous integrase, regulated by a first tissue specific promoter sequence, activated only in the target cell;
  (b) a second sequence encoding the exogenous gene of interest regulated by a second tissue specific promoter sequence activated only in the target cell; and
  (c) a sequence encoding a transcription terminator and located upstream to the sequence encoding the exogenous gene of interest,
wherein only in the presence of the expressed exogenous integrase, the transcription terminator is excised by site-specific excision, thereby enabling the expression of the exogenous gene of interest in the target cell.

According to some embodiments, the first and second sequences may be located on a single nucleic acid molecule. According to some embodiments, the first and second sequences may be located on separate nucleic acid molecules.

According to some embodiments the sequence encoding the transcription terminator is located between said second tissue specific promoter sequence and the sequence encoding for the exogenous gene of interest.

According to some embodiments, the first and second tissue specific promoters may be identical or different.

According to some embodiments, the transcription terminator is flanked by two recombination sites.

According to some embodiments, the sequence encoding the transcription terminator is inserted between an attL and an attR sequence.

According to some embodiments, the integrase is a site-specific recombinase selected from the group consisting of: Cre recombinase, Flp recombinase, bacteriophage lamda integrase, PhiC31 integrase, R4 integrase and HK022 integrase. Each possibility represents a separate embodiment of the invention.

According to some embodiments, the target cell is selected from the group consisting of: human cell, animal cell, cultured cell and plant cell.

According to some embodiments, the human cell is selected from the group consisting of cancer cells, hepatocytes, neuronal cells, bone cells, connective tissue cells, erythrocytes, lymphocytes, monocytes, megakaryocytes, granulocytes, hematopoietic stem cells, hematopoietic progenitor cells, dendritic cells, Langerhans cells, epithelial cells and fibroblasts.

According to some embodiments, at least one of the tissue specific promoters is a promoter activated in a cancer cell selected from the group consisting of: hTERT, DF3/MUC1, HE4, PSA, probasin, hK2 and MSLN promoters.

According to some embodiments the exogenous gene of interest encodes a toxin, wherein the toxin is selected from the group consisting of Diphteria toxin (DTA), *pseudomonas* exotoxin A, photosensitizer Killer Red protein and modified forms thereof.

According to some embodiments there is provided a pharmaceutical composition comprising as the active ingredient the composition of the invention.

According to some embodiments, the pharmaceutical composition further comprises at least one pharmaceutically acceptable excipient, carrier, and diluent.

According to some embodiments the pharmaceutical composition is administered by a route selected from systemic administration and topical administration.

According to some embodiments the pharmaceutical composition, is administered by a route selected from the group consisting of: enteral and parenteral administration.

According to some embodiments the pharmaceutical composition is administered by a route selected from the group consisting of: oral and rectal administration.

According to some embodiments the pharmaceutical is administered by a route selected from the group consisting of: transdermal administration and injection.

According to some embodiments the pharmaceutical composition, is administered by a route selected from the group consisting of: intravenous injection, intramuscular injection, and subcutaneous injection.

According to some embodiments, there is provided a method for the expression of an exogenous gene of interest in a target cell, the method comprising introducing the cell with a composition comprising:
  (a) a first sequence encoding an exogenous integrase, regulated by a first tissue specific promoter sequence;
  (b) a second sequence encoding an exogenous gene of interest regulated by a second tissue specific promoter sequence; and
  (c) a sequence encoding a transcription terminator located upstream to the sequence encoding the exogenous gene of interest;
wherein only in a cell expressing the exogenous integrase, the transcription terminator is excised by site-specific excision, thereby enabling the expression of the exogenous gene of interest in the target cell.

According to some embodiments the first and second tissue specific promoters are activated specifically in the target cell.

According to some embodiments the first and second tissue specific promoters may be identical or different.

According to some embodiments, the transcription terminator is flanked by at least two recombination sites.

According to some embodiments, there is provided a method for the targeted killing of a target cell, the method comprising introducing the cell with a composition comprising:
  (a) a first sequence encoding an exogenous integrase, regulated by a first tissue specific promoter sequence;
  (b) a second sequence encoding an exogenous toxin, regulated by a second tissue specific promoter sequence; and (c) a sequence encoding a transcription terminator located upstream to the sequence encoding the exogenous toxin, wherein only in a cell expressing the exogenous integrase, the transcription terminator is excised by site-specific excision, thereby enabling the expression of the toxin in the target cell.

According to some embodiments, there is provided a method for treating cancer, comprising administering to a subject in need of such treatment a composition comprising:
(a) a first sequence encoding an exogenous integrase, regulated by a first tissue specific promoter sequence;
(b) a second sequence encoding an exogenous toxin, regulated by a second tissue specific promoter sequence; and
(c) a sequence encoding a transcription terminator and located upstream to the sequence encoding the exogenous toxin, wherein only in a cell expressing the exogenous integrase, the transcription terminator is excised by site-specific excision, thereby enabling specific expression of the exogenous toxin in cancer cells of the subject.

According to some embodiments, the present invention provides a composition for the use of treating cancer, the composition comprising:
(a) a first sequence encoding an exogenous integrase, regulated by a first tissue specific promoter sequence;
(b) a second sequence encoding an exogenous toxin, regulated by a second tissue specific promoter sequence; and
(c) a sequence encoding a transcription terminator and located upstream to the sequence encoding the exogenous toxin, wherein specifically in the presence of the expressed integrase, the transcription terminator is excised by site-specific excision, thereby enabling specific expression of the exogenous toxin in cancer cells of the subject; thereby treating cancer.

According to some embodiments, the present invention provides a composition comprising:
(a) a first sequence encoding an exogenous integrase, regulated by a first tissue specific promoter sequence;
(b) a second sequence encoding an exogenous toxin, regulated by a second tissue specific promoter sequence; and
(c) a sequence encoding a transcription terminator and located upstream to the sequence encoding the exogenous toxin, wherein only in a cell expressing the exogenous integrase, the transcription terminator is excised by site-specific excision, thereby enabling specific expression of the exogenous toxin in cancer cells of the subject; for the use of treating cancer in a subject in need of such treatment.

Some embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 2, panel a shows the substrate comprising the loci of the attL×attR reaction, the termination transcription sequence (Stop), the sequence encoding the integrase, the hTERT promoters and the sequence encoding the DTA toxin or GFP. FIG. 2, panel b shows the expected recombination products;

FIG. 5C shows the mammary gland tumor in visible light;

FIGS. 6A-C shows pictograms of luminescence of various mice injected with various plasmids. FIG. 6A, is a pictogram of luminescence of mice injected W into the tail with a luciferase plasmid in conjunction with the In vivo jet PEI transfection reagent, following IP injection of luciferin. FIG. 6B is a pictogram of luminescence of a luciferase-transgenic mouse injected with luciferin. FIG. 6C is a pictogram of luminescence of a control mouse injected with luciferin;

DETAILED DESCRIPTION OF THE INVENTION

Figure 1:
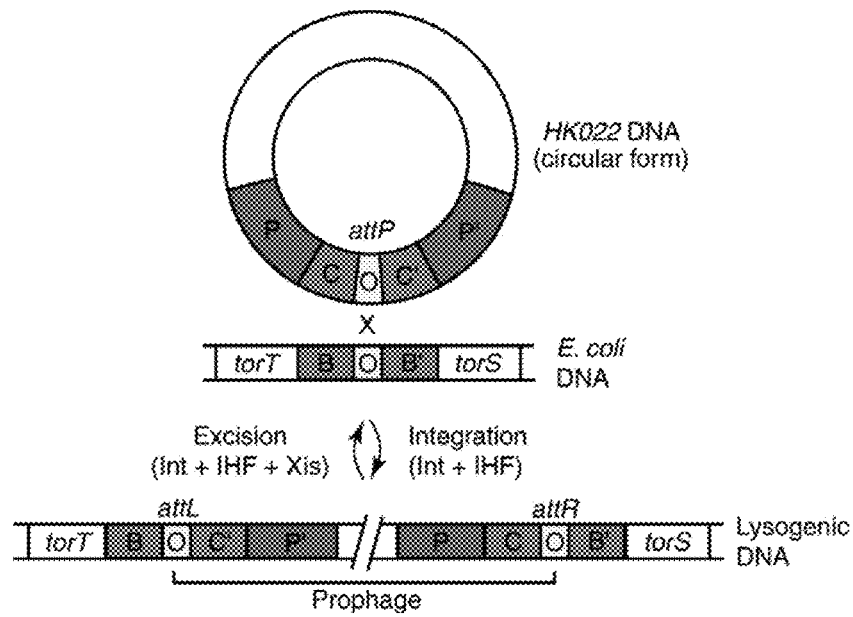
FIG. 1 is a schematic presentation of the integration and excision of phage HK022 into the *E. coli* DNA. The cross- over between attP (COC') and attB (BOB') results in a prophage flanked by the excision sites attL (BOP') and attR (POB')

The present invention provides compositions and methods for expressing an exogenous gene of interest by an exogenous integrase specifically in cells in which the exogenous integrase is expressed.

In the following detailed description of the invention when a reference term, such as: said, the, the last and the former; is used it refers to the exact term that is mentioned above (e.g. wherein said "The nucleic acid sequence" it refers to the nucleic acid sequence that is mentioned above). Furthermore, in the following detailed description of the invention each embodiment that refers to other embodiments is defined as a separate unit.

The following are terms which are used throughout the description and which should be understood in accordance with the various embodiments to mean as follows:

As referred to herein, the terms "polynucleotide molecules", "oligonucleotide", "polynucleotide", "nucleic acid" and "nucleotide" sequences may interchangeably be used herein. The terms are directed to polymers of deoxyribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucleotide or polynucleotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, shRNA, siRNA, miRNA, and the like. Accordingly, as used herein, the terms "polynucleotide molecules", "oligonucleotide", "polynucleotide", "nucleic acid" and "nucleotide" sequences are meant to refer to both DNA and RNA molecules. The terms further include oligonucleotides composed of naturally occurring bases, sugars, and covalent inter nucleoside linkages, as well as oligonucleotides having non-naturally occurring portions, which function similarly to respective naturally occurring portions.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As referred to herein, the term "complementarity" is directed to base pairing between strands of nucleic acids. As known in the art, each strand of a nucleic acid may be complementary to another strand in that the base pairs between the strands are non-covalently connected via two or three hydrogen bonds. Two nucleotides on opposite complementary nucleic acid strands that are connected by hydrogen bonds are called a base pair. According to the Watson-Crick DNA base pairing, adenine (A) forms a base pair with thymine (T) and guanine (G) with cytosine (C). In RNA, thymine is replaced by uracil (U). The degree of complementarity between two strands of nucleic acid may vary, according to the number (or percentage) of nucleotides that form base pairs between the strands. For example, "100% complementarity" indicates that all the nucleotides in each strand form base pairs with the complement strand. For example, "95% complementarity" indicates that 95% of the nucleotides in each strand from base pair with the complement strand. The term sufficient complementarity may include any percentage of complementarity from about 30% to about 100%.

The term "construct", as used herein refers to an artificially assembled or isolated nucleic acid molecule which may include one or more nucleic acid sequences, wherein the nucleic acid sequences may include coding sequences (that is, sequence which encodes for an end product), regulatory sequences, non-coding sequences, or any combination thereof. The term construct includes, for example, vectors but should not be seen as being limited thereto.

"Expression vector" refers to vectors that have the ability to incorporate and express heterologous nucleic acid fragments (such as DNA) in a foreign cell. In other words, an expression vector comprises nucleic acid sequences/fragments (such as DNA, mRNA, tRNA, rRNA), capable of being transcribed. Many viral, prokaryotic and eukaryotic expression vectors are known and/or commercially available. Selection of appropriate expression vectors is within the knowledge of those having skill in the art.

The term "exogenous" and exogenous gene", as used herein refers to nucleic acid sequences which are introduced to and/or expressed within a target cell. The exogenous nucleic acid sequences may be intact (that is, full-length sequences) or may be cleaved within the cell at one or more cleavage sites.

As used herein, the term "target cell" refers to any cell or group of cells such as but not limited to: human cells, animal cells, and plant cell into which the exogenous nucleic acid sequences are introduced.

As referred to herein, the terms "gene of interest" and "exogenous gene of interest", may interchangeably be used.

The terms refer to a nucleic acid sequence which may encode for any structural or functional molecule subsequently expressed in the target cell.

As referred to herein, the terms "protein of interest" and "exogenous protein of interest", may interchangeably be used. The terms refer to a peptide sequence which is translated from an exogenous RNA molecule, within a cell.

The terms "bacteriophage" and "phage" are used herein interchangeably and refer to a bacterial virus that infect bacteria, containing a DNA core and a protective shell comprising a number of different protein molecules. Typically, temperate bacteriophages infect bacteria by integrating the viral genome into the bacterial chromosome.

The terms "integrase", "recombination protein" and "site-specific recombinase" are used herein interchangeably and refer to any enzyme capable of performing the act of site specific recombination, including integrating/excising one nucleic acid sequence into or out of a specific chromosomal site.

The terms "recombination site", "recombination sequence" and "recombinase recognition site" are used herein interchangeably and refer to a recognition sequence on a nucleic acid molecule participating in an integration or recombination reaction by recombination proteins.

The terms "attL" and attR" refer to recombination sites flanking an integrated phage or any desired nucleic acid sequence. These att sequences are the substrates for excision recombination mediated by an integrase.

As used herein, the term "flanked" includes each end/side of a nucleic acid sequence. For example, a nucleic acid flanked by two recombination sites is directed to include a nucleic acid having a recombination site (identical or different) at each side (i.e. at the 3' end and at the 5' end of the nuclide acid). For example, a nucleic acid flanked by two recombination sites is directed to include a nucleic acid placed between two recombination sites (wherein the recombination sites may be identical or different). In some embodiments, more than one recombination sites may be located at each end/side of the nucleic acid.

The terms "site specific excision reaction", "excisive reaction" and "site specific excision" may interchangeably be used. The terms refer to the reaction mediated by the integrase in which a nucleic acid sequence (such as, for example, DNA) is excised out of a specific location from a larger nucleic acid sequence.

The terms "Upstream" and "Downstream", as used herein refers to a relative position in a nucleotide sequence, such as, for example, a DNA sequence or an RNA sequence. As well known, a nucleotide sequence has a 5' end and a 3' end, so called for the carbons on the sugar (deoxyribose or ribose) ring of the nucleotide backbone. Hence, relative to the position on the nucleotide sequence, the term downstream relates to the region towards the 3' end of the sequence. The term upstream relates to the region towards the 5' end of the strand.

As referred to herein, the term, "Open Reading Frame" ("ORF") is directed to a coding region which contains a start codon and a stop codon.

The terms "transcription terminator", "STOP" and "STOP codon" are used herein interchangeably and refer to a sequence that does not encode an amino acid such that the transcription is terminated. Typically, stop codons include, but are not limited to TAA, TAG and TGA. The transcription terminator is used in the present invention to prevent the expression of the exogenous gene of interest under any condition.

The terms "promoter element", "promoter" or "promoter sequence" as used herein, refer to a nucleotide sequence that is generally located at the 5' end (that is, precedes, located upstream) of the coding sequence and functions as a switch, activating the expression of a coding sequence. If the coding sequence is activated, it is said to be transcribed. Transcription generally involves the synthesis of an RNA molecule (such as, for example, an mRNA) from a coding sequence. The promoter, therefore, serves as a transcriptional regulatory element and also provides a site for initiation of transcription of the coding sequence into mRNA. Promoters may be derived in their entirety from a native source, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions, or at various expression levels. Promoters which cause a gene to be expressed in most cell types at most times are commonly referred to as "constitutive promoters". Promoters that derive gene expression in a specific tissue are called "tissue specific promoters".

The term "expression", as used herein, refers to the production of a desired end-product molecule in a target cell. The end-product molecule may include, for example an RNA molecule; a peptide or a protein; and the like; or combinations thereof.

As used herein, the terms "introducing" and "transfection" may interchangeably be used and refer to the transfer of molecules, such as, for example, nucleic acids, polynucleotide molecules, vectors, and the like into a target cell(s), and more specifically into the interior of a membrane-enclosed space of a target cell(s). The molecules can be "introduced" into the target cell(s) by any means known to those of skill in the art, for example as taught by Sambrook et al. (Sambrook et al., 1989), the contents of which are incorporated by reference herein. Means of "introducing" molecules into a cell include, for example, but are not limited to: heat shock, calcium phosphate transfection, Polyethylenimine (PEI) transfection, electroporation, lipofection, transfection reagent(s), viral-mediated transfer, and the like, or combinations thereof. The transfection of the cell may be performed on any type of cell, of any origin, such as, for example, human cells, animal cells, plant cells, and the like. The cells may include isolated cells, tissue cultured cells, cell lines, cells present within an organism body, and the like. Transfection may be "stable", where the introduced DNA is incorporated into the genome of the cell, or "transient", where the introduced DNA is not incorporated into the genome of the cell and may eventually disappear.

Expression vectors for stable expression of a polypeptide can be introduced into cells using transfection methods, as described above. Useful mammalian expression vectors and methods of introducing such vectors into mammalian cells either ex vivo or in vivo are well known in the art. Non-limiting examples include a plasmid expression vector which can be introduced into a cell by calcium-phosphate mediated transfection, DEAE dextran-mediated transfection, lipofection, polybrene- or polylysine-mediated transfection, electroporation, or by conjugation to an antibody, gramacidin S, or other intracellular carrier.

The term "Kill" with respect to a cell/cell population is directed to include any type of manipulation that will lead to the death of that cell/cell population.

As referred to herein, the term "Treating a disease" or "treating a condition" is directed to administering a composition, which includes at least one reagent (which may include, for example, one or more polynucleotide molecules, one or more expression vectors, one or more substance/ingredient, and the like), effective to ameliorate symptoms associated with a disease, to lessen the severity or cure the disease, or to prevent the disease from occurring. Administration may include any administration route.

The terms "Detection, "Diagnosis" refer to methods of detection of a disease, symptom, disorder, pathological or normal condition; classifying a disease, symptom, disorder, pathological condition; determining a severity of a disease, symptom, disorder, pathological condition; monitoring disease, symptom, disorder, pathological condition progression; forecasting an outcome and/or prospects of recovery thereof.

The term "only in a target cell" is directed to include essentially only in a target cell.

The present invention provides a composition comprising at least one nucleic acid sequence for expression of an exogenous gene of interest specifically in a target cell expressing an exogenous integrase, wherein said at least one nucleic acid sequence comprises:
  (a) a first sequence encoding the exogenous integrase, regulated by a first tissue specific promoter sequence, activated only in the target cell;
  (b) a second sequence encoding the exogenous gene of interest regulated by a second tissue specific promoter sequence activated only in the target cell; and
  (c) a sequence encoding a transcription terminator located upstream to the sequence encoding the exogenous gene of interest,
wherein only in a cell expressing the exogenous integrase, the transcription terminator is excised by site-specific excision, thereby enabling the expression of the exogenous gene of interest in the target cell.

According to some embodiments, the first and second nucleic acid sequences may be located on a single nucleic acid molecule.

According to some embodiments, the first and second nucleic acid sequences may be located on separate nucleic acid molecules.

According to some embodiments the sequence encoding the transcription terminator is located between the second tissue specific promoter sequence and the sequence encoding for the exogenous gene of interest.

According to some embodiments, the first and second tissue specific promoters may be identical or different.

According to some embodiments, the tissue-specific promoter regulates expression of a selected nucleic acid sequence operably linked to the promoter, and effects expression of the selected nucleic acid sequence in specific cells of a tissue. Non limiting examples of tissue specific promoters include muscular beta actin promoter, growth hormone regulatory promoter, a promoter under the control of lac operon sequence, an antibiotic-inducible promoter, a prion protein promoter, neuron-specific promoter and a zinc-inducible metallothionein promoter.

According to some embodiments at least one of the tissue specific promoter is a promoter activated in a cancer cell selected from the group consisting of: hTERT, DF3/MUC1, HE4 and MSLN promoters.

According to some embodiments, the transcription terminator is flanked by at least two recombination sites.

The sequence encoding the transcription terminator is inserted between an attL and an attR sequence, thereby forming a recombination site, which subsequently enables the excision of the transcription terminator, mediated by the integrase.

The recombination site serves as a recognition sequence on a nucleic acid molecule participating in an integration or recombination reaction by recombination proteins. For example, the recognition sequence for Cre recombinase is loxP which is a 34 base pair sequence comprised of two 13 base pair inverted repeats (serving as the recombinase binding sites) flanking an 8 base pair core sequence. Other non limiting examples of recognition sequences include the attB, attP, attL, and attR sequences described herein, and mutants, fragments, variants and derivatives thereof. These sequences are recognized by the recombination protein integrase and optionally by additional proteins such as integration host factor (IHF), factor for inversion specificity (FIS) and excisionase (Xis). Typically, the sequence attB is approximately 25 base pair in length comprising two 9 base pair core-type integrase binding sites and a 7 base pair overlap region. The attP sequence is approximately 240 base pair in length comprising core-type integrase binding sites that flank the overlap sequence and arm-type integrase binding sites as well as sites for assisting proteins such as IHF, FIS and Xis. Such sites may be engineered according to the teachings of the present invention to enhance site specific excision, thereby enabling the compositions and methods disclosed in the present invention.

Typically, a phage encodes for an integrase which mediates recombination between the phage attachment site, attP, and the bacterial attachment site, attB. Following integration, the integrated phage is flanked by the attL and attR sequences, each comprising half of the attP sequence and half of the attB sequence. The hybrid att sequences are the substrates for excisive recombination mediated by the integrase, optionally with additional factors.

In some exemplary embodiments, the attL is the attL of the Lambda genome (accession number NC_001416, nucleotide position nt 27,724-27,781). In some exemplary embodiments, the attR is the attR of the Lambda genome (accession number NC_001416, nucleotide position nt 27,571-27,742). In some exemplary embodiments, the attP is the attP of the Lambda genome (accession number NC_001416, nucleotide position nt 27571-27813). In some exemplary embodiments, the attB is the *E. Coli* corresponding site to the Lambda attP site.

According to some embodiments, the integrase is selected from the group consisting of bacteriophage lambda integrase, PHIC31 integrase, R4 integrase and HK022 integrase.

According to some embodiments, there is provided a composition comprising a nucleic acid sequence for expression of an exogenous gene of interest essentially only in a target cell expressing the exogenous integrase, wherein the nucleic acid sequence comprises (a) sequence encoding for the exogenous integrase, regulated by a first tissue specific promoter sequence, activated only in the target cell; (b) a sequence encoding for the exogenous gene of interest regulated by a second tissue specific promoter sequence activated only in the target cell; and (c) a sequence encoding a transcription terminator located upstream to the sequence encoding the exogenous gene of interest; wherein only in the presence of the expressed integrase, the transcription terminator is excised by site-specific excision, thereby enabling the expression of the exogenous gene of interest in the target cell.

The present invention provides compositions and methods for the expression of an exogenous gene in a target cell. According to some embodiments, the cell is a primary cell, tissue culture cell, cell line, and the like. In some embodiments the cell may be any cell or group of cells present in a subject including single cells and populations of cells. In some embodiments the target cell is selected from the group consisting of: human cell, animal cell, cultured cell and plant cell.

According to some embodiments, the human cell may be selected from the group consisting of cancer cells, hepatocytes, neuronal cells, bone cells, connective tissue cells, erythrocytes, lymphocytes, monocytes, megakaryocytes, granulocytes, hematopoietic stem cells, hematopoietic progenitor cells, dendritic cells, Langerhans cells, epithelial cells and fibroblasts.

According to some embodiments, the target cell may refer to a cancer cell which may or not be part of a tumor. Thus, the target cell may be present in a tissue of an inflammatory lesion and a tumor. In some embodiments the tumor is selected from the group consisting of a primary tumor, a metastasized tumor a carcinoma, colon adenocarcinoma, an esophageal tumor, a bladder tumor, a breast tumor, a pancreatic tumor, a lung tumor, a gastric tumor, a hepatic tumor, a head and/or neck tumor, a cervical tumor, an endometrial tumor, and a skin tumor.

According to some embodiments, the exogenous gene of interest may encode for any structural or functional molecule, such as, for example, a protein, a nucleic acid, and the like. For example, the exogenous gene of interest may encode a protein selected from, but not limited to: an enzyme, a receptor, a hormone, a growth factor, a signaling protein, a transporter, a DNA binding protein, a chaperone protein, a toxin, a fluorescent protein, an antibody, or the like.

A non-limiting example of an enzyme which the exogenous gene of interest may encode for is the enzyme factor IX. Targeted expression of factor IXsolely in liver tissue, using the methods of the invention (i.e. use of tissue specific promoters expressed solely in liver cells), may be used to treat diseases associated with decreased liver function, to support liver regeneration, detoxification, metabolism of various substances and the like.

According to some embodiments the exogenous gene of interest may encode for a toxin, capable of killing or affecting the target cell. The composition of the invention comprising the toxin sequence as the exogenous gene of interest, in combination with tissue specific promoters as described herein, can be used to target and destroy, any target cell. A number of toxin proteins are known and can be used in the present invention, including but not limited to: diphteria toxin A (DTA), ribosome inactivators, *pseudomonas* exotoxin A, cell metabolism disruptors, such as ribonucleases, vamase toxin, pertussis, cholera ricin, photosensitizer Killer Red protein and modified forms thereof.

The present invention also provides for pharmaceutical compositions comprising an effective amount of the composition of the invention and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "Carrier" refers to a diluent, adjuvant, excipient, or vehicle with which the therapeutic is administered.

According to some embodiments, the pharmaceutical composition may be administered to a subject in need by any administration route known, such as, for example but not limited to: enteral, parenteral, injection, topical, and the like. In some embodiments, it may be desirable to administer the pharmaceutical compositions of the invention locally to a target area in need of treatment. This may be achieved by, for example, but not limited to: local infusion during surgery, topical application, (for example, in conjunction with a wound dressing after surgery), by injection, by means of a catheter, by means of a suppository, or by means of an implant, said implant being of a porous, non-porous, or gelatinous material, including membranes, such as sialastic membranes, or fibers. The local administration may also be achieved by controlled release drug delivery systems, such as nanoparticles, matrices such as controlled-release polymers or hydrogels.

In some embodiments, the composition of the invention may be administered in amounts which are effective to produce the desired effect in the targeted cell/tissue. Effective dosages of the composition of the invention may be determined through procedures well known to the skilled in the art which address such parameters as biological half-life, bioavailability and toxicity. The amount of the composition of the invention which is effective, depends on the nature of the disease or disorder being treated, and can be determined by standard clinical techniques. In addition, in vitro assays may optionally be employed to help identify optimal dosage ranges. The administered means may also include, but are not limited to permanent or continuous injection of the composition of the invention to the patient blood stream.

In some embodiments, the composition, and the pharmaceutical composition comprising same, may be administered to various organisms, such as, for example, mammals, avian, plants, and the like. For example, the composition, and the pharmaceutical composition comprising same, may be administered to humans, and animals.

According to some embodiments, the present invention also provides a pharmaceutical pack or kit comprising one or more containers filled with one or more of the ingredients of the pharmaceutical compositions of the invention. Optionally, associated with such container(s) can be a notice in the form prescribed by a governmental agency regulating the manufacture, use or sale of pharmaceuticals or biological products, which notice reflects approval by the agency of manufacture, use or sale for human or animal administration. According to some embodiments, the pharmaceutical composition further comprises at least one pharmaceutically acceptable excipient, carrier, and diluent.

According to some embodiments, the present invention further provides a method for the targeted killing of a target cell, the method comprising introducing into the cell a composition comprising:
(a) a first sequence encoding an exogenous integrase, regulated by a first tissue specific promoter sequence;
(b) a second sequence encoding an exogenous toxin, regulated by a second tissue specific promoter sequence; and
(c) a sequence encoding a transcription terminator located upstream to the sequence encoding the exogenous toxin;
wherein only in the presence of the expressed integrase, the transcription terminator is excised by site-specific excision, thereby enabling the expression of the toxin in the target cell.

According to some embodiments, the transcription terminator is flanked by two recombination sites in tandem.

The target cell may be a cancer cell, including but not limited to: breast cancer cell, a colorectal cancer cell, a lung cancer cell, an ovarian cancer cell, a central nervous system cancer cell, a liver cancer cell, a bladder cancer cell, a pancreatic cancer cell, a cervical cancer cell, a melanoma cell and a leukemia cell.

According to some embodiments of the invention, the target cell may stably express the exogenously expressed genes, namely the exogenous integrase and the exogenous gene of interest.

The composition of the invention comprising the toxin sequence can be used to target and destroy any target cell. Toxin proteins that may be used in the present invention, include such toxins as, but not limited to: diphteria toxin A (DTA), ribosome inactivators, *pseudomonas* exotoxin A, cell metabolism disruptors, such as ribonucleases, vamase toxin, pertussis, cholera ricin, photosensitizer Killer Red protein and modified forms thereof.

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

Example 1: HK022 Integrase-Dependent Expression Vectors of dta/Green Fluorescent Protein (GFP)

Figure 2:
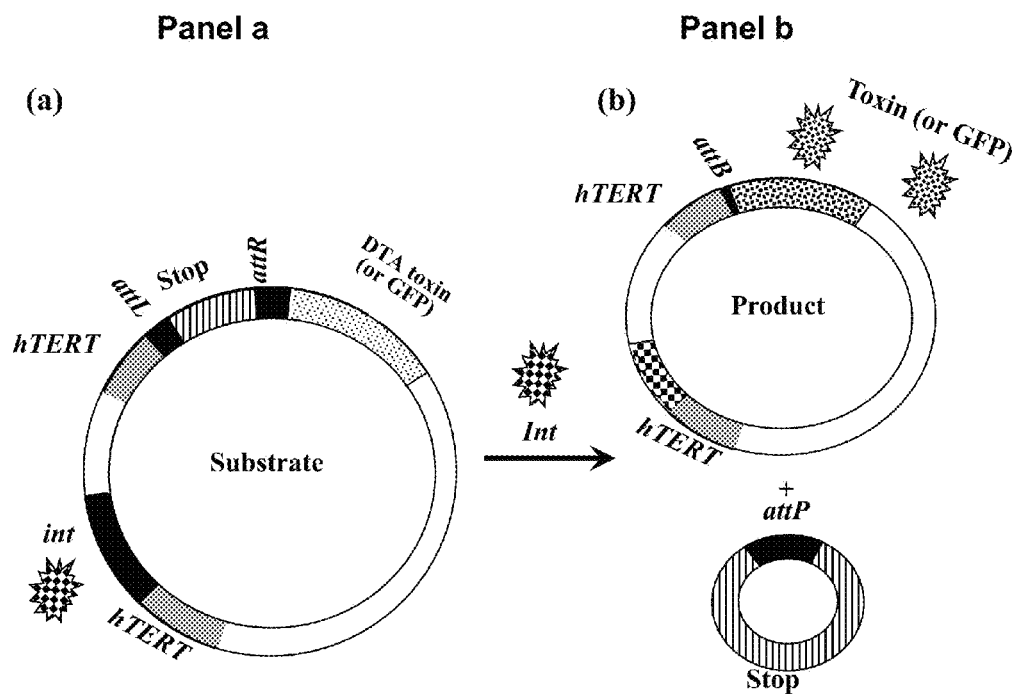
FIG. 2 is a schematic presentation of the recombination reactions.

The HK022 integrase-dependent expression vector of the invention, pHTERT-int-pHTERT-attR-Stop-attL-dta, comprises an attL-Stop-attR recombination cassette (FIG. 1) inserted between the hTERT promoter and the open reading frame of the diphteria toxin (dta) gene (FIG. 2, Panel a). The "Stop" sequence, located up-stream to the dta gene, prevents the expression of the gene. Upstream to the hTERT promoter controlling the dta gene is the integrase (int) gene, also under the control of an hTERT promoter. The hTERT promoter controlling the dta and the int genes is activated only in cancer cells expressing hTERT. When expressed, the integrase excises the Stop terminator by a site-specific excision (FIG. 2, Panel b) which subsequently allows the expression of the DTA toxin.

A green fluorescent protein (GFP) reporter replacing the dta gene is used when monitoring the expression level (FIG. 2, Panel a).

Example 2: Toxicity of DTA in Human Cells

Figure 3:
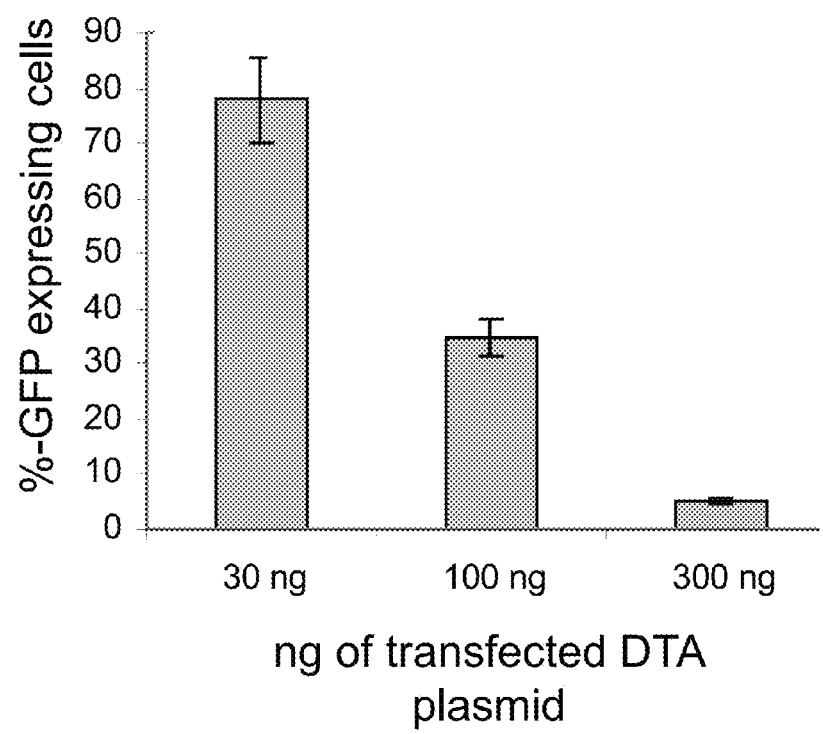
FIG. 3 is a bar graph demonstrating the DTA toxicity in human cells and its capability of killing cancer cells.

It has been shown by some of the inventors of the present invention, that the integrase HK022 can catalyze site-specific recombination reactions on the chromosomal level in human cell culture, including integrative as well as excisive reactions. In order to assess toxicity of DTA in human cells, the construct including the int and the dta genes were cloned under the constitutive CMV promoter. DTA expression was calibrated and its toxicity measured in human immortalized cells (line HEK293) that are considered to be cancerous (ATCC Catalog No. CRL-1573). The cells were co-transfected with increasing amounts of the plasmid expressing the dta gene, together with a GFP expressing plasmid. FIG. 3 shows the percentage of GFP expressing cells, as monitored by FACS, in co-transfected cells relative to cells transfected with GFP alone (co-transfected cells with (GFP and DTA plasmids) normalized to cells transfected with GFP alone). The results obtained show that transfection with 300 ng of the DTA plasmid leaves only 5% of the transfected cells, indicating that 95% of the cells were killed due to expression of DTA. Co-transfection with 30 ng of the DTA plasmid, leaves about 77.8% of the cells unaffected.

Example 3: Specificity of the hTERT Promoter to Cancer Cells

In order to assess the specificity of the hTERT promoter to cancer cells, the activity of the HK022 int gene regulated by the hTERT promoter in the immortalized (cancer) cell line (HEK293) was compared to that of the normal fibroblast cell line (BJ, ATCC Catalog No. CRL-2522). Each of the two cell lines were co-transfected with a pCMV-attR-Stop-attL-GFP reporter plasmid together with either of the two integrase expressing plasmids, namely the hTERT-Int or the CMV-Int plasmids. The Integrase catalyzes the attL×attR recombination and allows GFP expression which was monitored by FACS.

Figure 4:
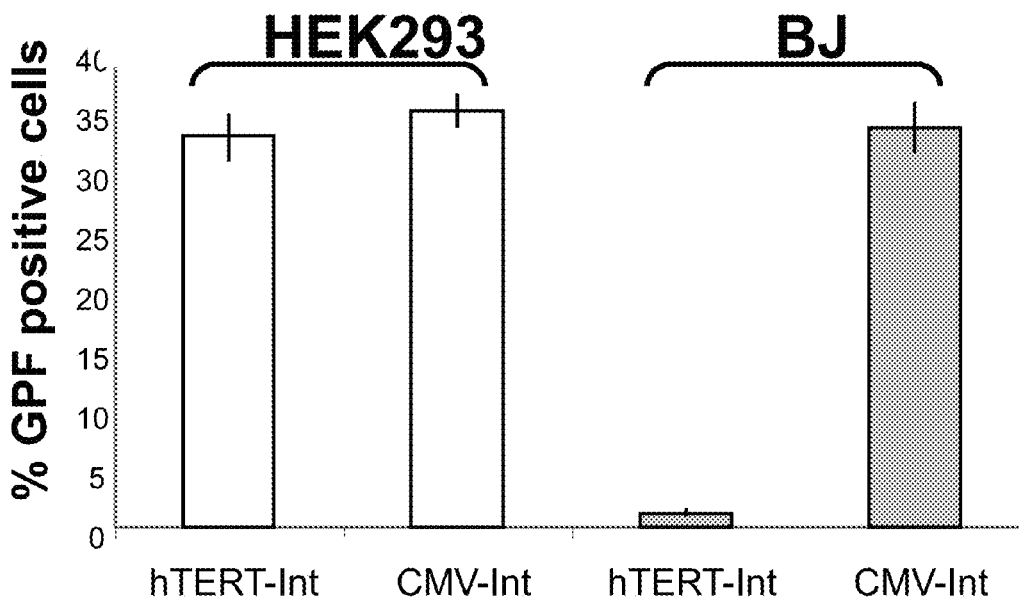
FIG. 4 is a bar graph demonstrating the recombination activity of integrase regulated by the hTERT, or the CMV promoter in cancer cells (HEK293) and normal fibroblast cells (BJ)

As seen in FIG. 4, in the immortalized cell line (HEK293), the integrase was active both when regulated by the CMV promoter and when regulated by the hTERT promoter, whereas in the normal cells (BJ) only the constitutive CMV-promoter activated the integrase and consequently facilitated GFP expression. Hence, the activity of the hTERT promoter was shown to be highly specific to cancer cells, and only negligible leakage was observed in non-cancerous cells, even when only the Int gene was regulated by the hTERT promoter.

Figure 5A:
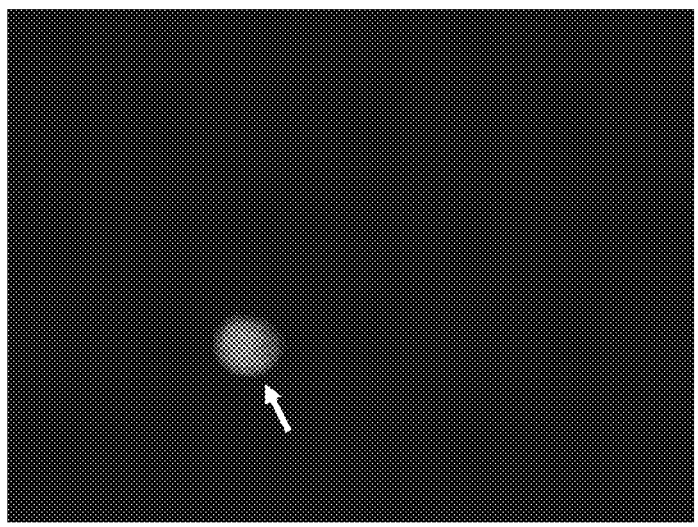
FIGS. 5A-C, show pictograms of fluorescence of solid tumors induced by the injection of DA3 mCherry cells into the mammary gland (arrow, FIG. 5A) or shoulder bone area (FIG. 5B, arrows).
Figure 5B:
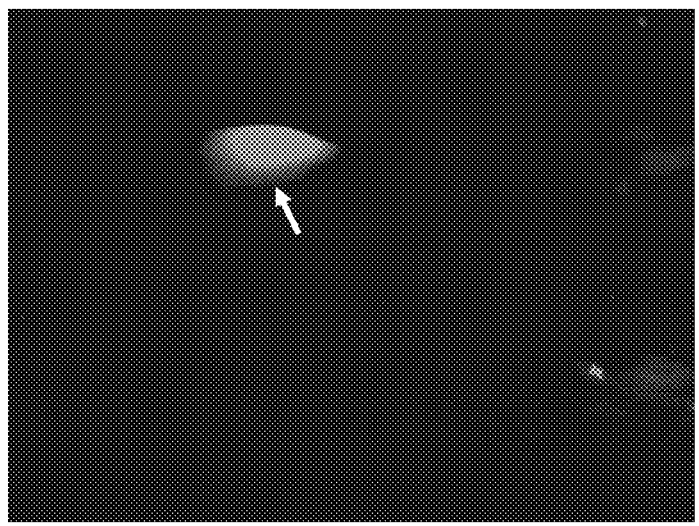
Figure 5C:
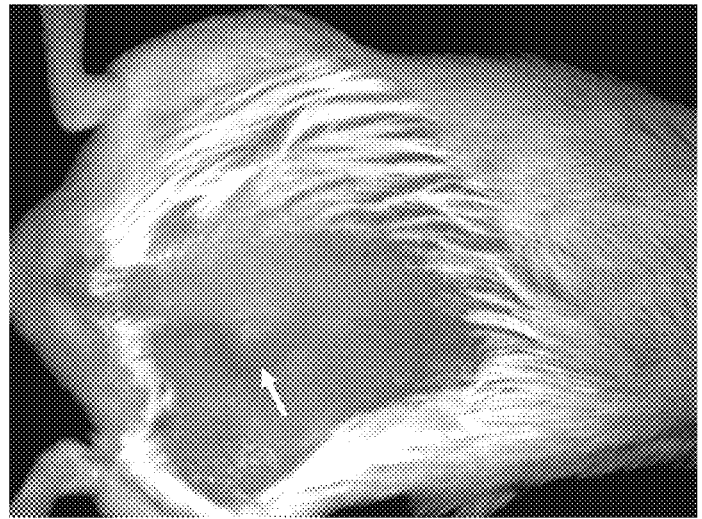

Example 4: Development of an Experimental Mouse Model Allowing Monitoring Cancer Cells BALB/c mice were injected with DA3 cells carrying the mCherry fluorescence reporter gene (DA3mCherry). These cells are well-characterized tumor-inducing cells derived from the D1-DMBA-3 mammary tumor syngeneic to BALB/c mice (Sotomayor et al., 1991). 1×10$^6$ DA3mCherry cells were injected subcutaneously into either the mammary gland or the shoulder bone area. 5-7 days later, solid tumor tissues developed in both areas of injection (FIG. 5). Hence, developed is an experimental model of mammary cancer in the mouse mammary gland and shoulder bone area. This experimental model facilitates the assessment of Int-promoted induction of the exogenously introduced diphtheria toxin gene (as described in Example 1) as well as tumor cell specific apoptosis as a result thereof.

Example 5: Delivery and Expression of Exogenously Introduced DNA in Mice Using the In Vivo-Jet PEI Transfection Agent In vivo jet PEI (Polyplus) is a linear polyethylenimine used for effective and reproducible in vivo delivery of nucleic acids (Polyplus Tranfection™). BALB/c mice were intravenously injected with a reporter plasmid carrying the luciferase reporter (luc) gene under the CMV promoter in conjunction with the In vivo jet PEI transfection agent according to manufacture's instructions. 24 hours later the mice were injected intra-peritoneally with the luciferase substrate luciferin, and the luminescence of the mice was assessed using a Biospace imager. As seen from FIG. 6A a notable luminescence was obtained in mice in which the luciferase gene was introduced using the In vivo jet PEI transfection agent (FIG. 6A) when compared to that of a luciferase-transgenic mouse serving as a positive control (FIG. 6B) and to a control mouse injected with luciferin serving as a negative control (FIG. 6C). This demonstrates that the In vivo jet PEI transfection reagent can serve as a mean for, the intravenous or intratumoral delivery of DNA molecules to mouse cancer cells.

Figure 7A:
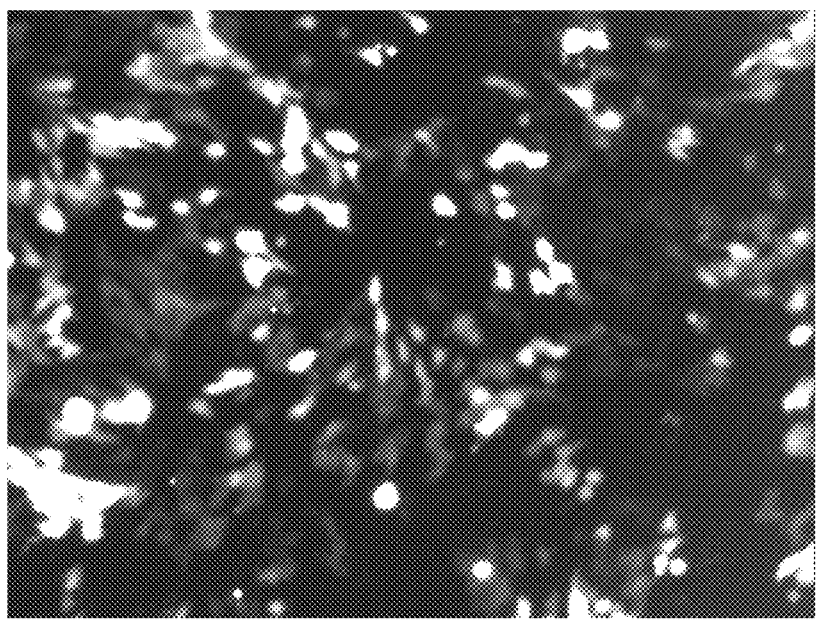
FIG. 7A shows image of a view field obtained by fluorescence microscopy detecting GFP expression in DA3 cells infected with LentiGFP virus.
Figure 7B:
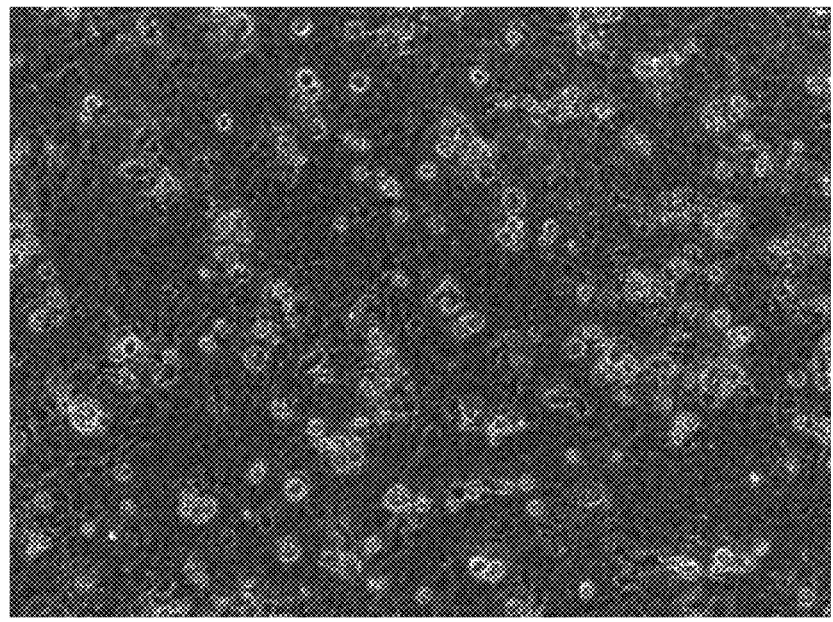
FIG. 7B shows an image of the view field of the infected DA3 cells under visible light.

Example 6: Delivery and Expression of Exogenously Introduced DNA in Cancer Cells Using a Lentiviral Vector Lentiviral vectors allow for stable long-term transgenic expression in cells and tissues. A lentiviral vector carrying the GFP gene regulated by the CMV promoter (LentiGFP, unpublished) was used to infect the tumor-generating DA3 cells. GFP expression (infection efficiency) was assessed 48 hours post infection using fluorescence microscopy. The significant fluorescence obtained (FIG. 7A) illustrate that the lentiviral delivery system can serve as an efficient experimental system for the assessment of the toxic effect of exogenous gene expression such as, for example, Int-induced expression of the exogenously introduced diphtheria toxin (DTA) gene.

Example 7: Delivery and Expression of Exogenously Introduced DNA in Mice Using a Lentiviral Vector BALB/c mice are injected with DA3 cells carrying the mCherry fluorescence reporter gene (as described in example 4). When the tumor reaches 0.5-0.7 cm in diameter (7-10 day later) the mice are intra-tumorally injected with Lenti-viruses carrying the GFP gene under either a CMV or a hTERT promoter. Mice are sacrificed at different time points after injection and single-cell suspension are prepared from the tumor tissues. Fluorescence is measured using a FACS flow cytometer. GFP expression in cells infected with GFP regulated either by the CMV promoter or the hTERT promoter is compared in order to assess the specificity toward cancer cells.

Example 8: Cancer Specific Cell Death Following Int-Induced Expression of the Exogenously Expressed Diphtheria Toxin Gene in Mice BALB/c mice are injected with DA3 cells carrying the mCherry fluorescence reporter gene (as described in example 4). When the tumor reaches 0.5-0.7 cm in diameter (7-10 day later) the mice are intra-tumorally injected with either Lenti-viruses carrying the pHTERT-int-pHTERT-attR-Stop-attL-dta cassette (described in example 1) or with the pHTERT-int-pHTERT-attR-Stop-attL-dta cassette in conjunction with the In vivo-Jet PEI transfection agent. Mice are sacrificed at different time points after injection and single-cell suspension are prepared from the tumor tissues. Apoptosis of the tumor cells is measured by staining with FITC-conjugated Annexin-V and PI (PharMingen) and by TUNEL assay using Apo-Direct kit (PharMingen). Non-tumor tissues of the cancerous mice as well as cells from non-tumorized mice serve as negative controls. At least three mice are analyzed at each time point.

REFERENCES

Azaro, M. A., and Landy, A. (2002) Integrase and the λ int family. In Mobile DNAII. Craig, N. L., Craigie, R., Gellert, M., and Lambowitz, A. (eds). Washington D.C.: ASM Press, pp. 118-148.

Gottfried, P, Lotan, O, Kolot, M, Maslenin, L, Bendov, R, Gorovits, R et al (2005). Site-specific recombination in Arabidopsis plants promoted by Integrase protein of coliphage HK022. *Plant Molecular Biology* 57: 435-444.

Harel-Levy G., Goltsman J., Tuby C. N. J. H., Yagil E., and Kolot, M (2008) Human genomic site-specific recombination catalyzed by coliphge HK022 integrase. *J Biotechnol* 134: 45-54.

Malchin, N, Goltsman, J, Dabool, L, Gorovits, R, Bao, Q, Droge, P et al. (2009) Optimization of coliphage HK022 Integrase activity in human cells. *Gene* 437: 9-13.

Melnikov, O, Zaritsky, A, Zarka, A, Boussiba, S, Malchin, N, Yagil, E, and Kolot, M (2009) Site-Specific Recombination in the Cyanobacterium *Anabaena* sp Strain PCC 7120 Catalyzed by the Integrase of Coliphage HK022. *Journal of Bacteriology* 191: 4458-4464.

Sambrook, J., Fritsch, E. F., and Maniatis, T. (1989) Molecular cloning: a laboratory manual Cold Spring Harbor, N.Y.: Cold Spring Harbor Laboratory.

Sotomayor, E M, Fu, Y X, Lopezcepero, M, Herbert, L, Jimenez, J J, Albarracin, C, and Lopez, D M (1991) Role of Tumor-Derived Cytokines on the Immune-System of Mice Bearing A Mammary Adenocarcinoma 0.2. Down-Regulation of Macrophage-Mediated Cytotoxicity by Tumor-Derived Granulocyte-Macrophage Colony-Stimulating Factor. *Journal of Immunology* 147: 2816-2823.

Weisberg, R A, Gottesmann, M E, Hendrix, R W, and Little, J W (1999) Family values in the age of genomics: comparative analyses of temperate bacteriophage HK022. *Annu Rev Genet* 33: 565-602.

The invention claimed is:

1. A composition for transient expression of an exogenous protein of interest specifically in a human cancer cell, comprising at least one nucleic acid molecule, wherein said at least one nucleic acid molecule comprises:
   (a) a first nucleotide sequence encoding an exogenous HK022 integrase and including a first tissue specific promoter sequence operably linked to said sequence encoding said exogenous HK022 integrase, said first tissue specific promoter being capable of activating expression specifically in a human cancer cell and being selected from the group consisting of hTERT, DF3/MUC1, HE4, and MSLN promoters;
   (b) a second nucleotide sequence encoding the exogenous protein of interest and including a second tissue specific promoter sequence operably linked to said sequence encoding the exogenous protein of interest, said second tissue specific promoter being capable of activating expression specifically in a human cancer cell and being selected from the group consisting of hTERT, DF3/MUC1, HE4, and MSLN promoters; and
   (c) a third nucleotide sequence comprising a transcription terminator, an attL sequence and an attR sequence, said transcription terminator being located between the attL and attR sequences, said third nucleotide sequence being located upstream of the sequence encoding the exogenous protein of interest and between said sequence encoding the exogenous protein of interest and the second tissue specific promoter sequence.

2. The composition of claim 1, wherein the exogenous protein of interest is a toxin.

3. The composition of claim 2, wherein the toxin is selected from the group consisting of Diphteria toxin (DTA), *pseudomonas* exotoxin A, photosensitizer Killer Red protein and modified forms thereof.

4. A pharmaceutical composition comprising as the active ingredient the composition of claim 1 and at least one of a pharmaceutically acceptable excipient, carrier, and diluent.

5. The pharmaceutical composition of claim 4, formulated for enteral, parenteral, or topical administration.

6. The composition of claim 1, wherein the first tissue specific promoter and the second tissue specific promoter have an identical sequence.

7. The composition of claim 1, wherein the first tissue specific promoter and the second tissue specific promoter have different sequences.

8. The composition of claim 1, wherein at least one of said first and second tissue specific promoters is hTERT.

9. The composition of claim 8, wherein both said first and said second tissue specific promoters are hTERT.

10. A method for the expression of an exogenous protein of interest specifically in a human cancer cell, the method comprising introducing into the cell the composition of claim 1.

11. The method of claim 10, wherein the first tissue specific promoter and the second tissue specific promoter have an identical sequence.

12. The method of claim 10, wherein the first tissue specific promoter and the second tissue specific promoter have a different sequence.

13. A method for the targeted killing of a human cancer cell, the method comprising introducing into the cell the composition of claim 1, wherein the exogenous protein of interest is a toxin.

14. The method of claim 13, wherein the toxin is selected from the group consisting of Diphteria toxin (DTA), *pseudomonas* exotoxin A, photosensitizer Killer Red protein and modified forms thereof.

15. The method of claim 13, wherein the first tissue specific promoter and the second tissue specific promoter have an identical sequence.

16. The method of claim 13, wherein the cancer cell is harbored in a subject and the specific expression of the toxin in the cancer cell is used for treating cancer in said subject.

17. The method of claim 13, wherein the first tissue specific promoter and the second tissue specific promoter have a different sequence.

* * * * *